US010620194B2

(12) United States Patent
Andersson et al.

(10) Patent No.: US 10,620,194 B2
(45) Date of Patent: *Apr. 14, 2020

(54) CHARACTERIZATION OF REACTION VARIABLES

(71) Applicant: Gyros Patent AB, Uppsala (SE)

(72) Inventors: Per Andersson, Uppsala (SE); Mats Inganas, Uppsala (SE); Gunnar Thorsén, Hagersten (SE); Gunnar Kylberg, Bromma (SE)

(73) Assignee: GYROS Patent AB, Uppsala (SE)

( * ) Notice: Subject to any disclaimer, the term of this patent is extended or adjusted under 35 U.S.C. 154(b) by 886 days.

This patent is subject to a terminal disclaimer.

(21) Appl. No.: 14/215,745

(22) Filed: Mar. 17, 2014

(65) Prior Publication Data
US 2014/0199783 A1 Jul. 17, 2014
US 2015/0377873 A9 Dec. 31, 2015

Related U.S. Application Data

(63) Continuation of application No. 12/794,915, filed on Jun. 7, 2010, now abandoned, which is a continuation (Continued)

(30) Foreign Application Priority Data

Mar. 19, 2001 (SE) .................................... 0100951
Mar. 19, 2001 (SE) .................................... 0100952
Sep. 17, 2001 (SE) .................................... 0103117
Jan. 28, 2002 (SE) .................................... 0200242

(51) Int. Cl.
G01N 33/543 (2006.01)
B01F 5/06 (2006.01)
(Continued)

(52) U.S. Cl.
CPC ..... *G01N 33/54306* (2013.01); *B01F 5/0646* (2013.01); *B01F 5/0647* (2013.01);
(Continued)

(58) Field of Classification Search
CPC ....... G01N 33/54306; G01N 33/54366; G01N 35/00069; G01N 30/6095; G01N 30/7266; G01N 2035/00504; B01F 5/0646; B01F 5/0647; B01F 5/0655; B01F 13/0059; B01J 19/0093; B01J 2219/00788; B01J 2219/00833; B01J 2219/0086; B01J 2219/00862; B01J 2219/00891; B01L 3/5025; B01L 3/5027; B01L 3/502738; B01L 3/502746; B01L 2200/06; B01L 2200/0605; B01L 2200/10; B01L 2200/142; B01L 2300/069; B01L 2300/0803; B01L 2300/0806; B01L 2300/0861; B01L 2300/0864; B01L 2300/0867;
(Continued)

(56) References Cited

U.S. PATENT DOCUMENTS 3,852,595 A   12/1974  Aberth
4,018,652 A    4/1977  Lanham et al.
(Continued)

FOREIGN PATENT DOCUMENTS

EP   0073513 A1   3/1983
EP   0073513 B1   7/1985
(Continued)

OTHER PUBLICATIONS

Ahn et al., "A Fully Intergrated Micromachined Magnetic Particle Manipulator and Separator," Microelectronics Research center, School of Electrical and Computer Engineering: Georgia Institute of technology, Atlanta, GA; pp. 91-96.

Eteshola et al.; Development and characterization of an ELISA assay in PDMS microfluidic channels; Sensors and Actuators B 72:129-133, 2001.

Handique et al., "Microfluidic Flow Control Using Selective Hydrophobic Patterning", SPIE vol. 3224, 1992, pp. 185-195.

Kido et al., "Disc-based Immunoassay Microrrays," Analytica Chimica Acta, Elsevier Science B.V., 2000, pp. 1-11.

(Continued)

*Primary Examiner* — Andrea S Grossman
(74) *Attorney, Agent, or Firm* — Norton Rose Fulbright US LLP

(57) ABSTRACT

A microscale method for the characterization of one or more reaction variables that influence the formation or dissociation of an affinity complex comprising a ligand and a binder, which have mutual affinity for each other. The method is characterized in comprising the steps of: (i) providing a microfluidic device comprising a microchannel structures that are under a common flow control, each microchannel structure comprising a reaction microactivity; (ii) performing essentially in parallel an experiment in each of two or more of the plurality of microchannel structures, the experiment in these two or more microchannel structures comprising either a) formation of an immobilized form of the complex and retaining under flow conditions said form within the reaction microactivity, or b) dissociating, preferably under flow condition, an immobilized form of the complex which has been included in the microfluidic device provided in step (i), at least one reaction variable varies or is uncharacterized for said two or more microchannel structures while the remaining reaction variables are kept essentially constant; (iii) measuring the presentation of the complex in said reaction microactivity in said two or more microchannel structures; and (iv) characterizing said one or more reaction variables based on the values for presentation obtained in step (iii).

14 Claims, 5 Drawing Sheets

Related U.S. Application Data of application No. 10/472,421, filed as application No. PCT/SE02/00537 on Mar. 19, 2002, now Pat. No. 7,759,067, which is a continuation-in-part of application No. 09/811,741, filed on Mar. 19, 2001, now Pat. No. 6,653,625, and a continuation-in-part of application No. 09/812,123, filed on Mar. 19, 2001, now Pat. No. 6,717,136.

(60) Provisional application No. 60/322,621, filed on Sep. 17, 2001.

(51) Int. Cl.
   - *B01L 3/00* (2006.01)
   - *G01N 35/00* (2006.01)
   - *B01F 13/00* (2006.01)
   - *B01J 19/00* (2006.01)
   - *H01J 49/04* (2006.01)
   - *G01N 30/60* (2006.01)
   - *G01N 30/72* (2006.01)

(52) U.S. Cl.
   CPC ........ *B01F 5/0655* (2013.01); *B01F 13/0059* (2013.01); *B01J 19/0093* (2013.01); *B01L 3/5025* (2013.01); *B01L 3/5027* (2013.01); *B01L 3/502738* (2013.01); *B01L 3/502746* (2013.01); *G01N 33/54366* (2013.01); *G01N 35/00069* (2013.01); *H01J 49/04* (2013.01); *B01J 2219/0086* (2013.01); *B01J 2219/00788* (2013.01); *B01J 2219/00833* (2013.01); *B01J 2219/00862* (2013.01); *B01J 2219/00891* (2013.01); *B01L 2200/06* (2013.01); *B01L 2200/0605* (2013.01); *B01L 2200/10* (2013.01); *B01L 2200/142* (2013.01); *B01L 2300/069* (2013.01); *B01L 2300/0803* (2013.01); *B01L 2300/0806* (2013.01); *B01L 2300/087* (2013.01); *B01L 2300/0861* (2013.01); *B01L 2300/0864* (2013.01); *B01L 2300/0867* (2013.01); *B01L 2300/14* (2013.01); *B01L 2300/16* (2013.01); *B01L 2400/0406* (2013.01); *B01L 2400/0409* (2013.01); *B01L 2400/0633* (2013.01); *B01L 2400/0688* (2013.01); *B01L 2400/086* (2013.01); *G01N 30/6095* (2013.01); *G01N 30/7266* (2013.01); *G01N 2035/00504* (2013.01); *Y10S 435/973* (2013.01)

(58) Field of Classification Search
   CPC ........ B01L 2300/087; B01L 2300/014; B01L 2300/16; B01L 2400/0406; B01L 2400/0409; B01L 2400/0633; B01L 2400/0688; B01L 2400/086; H01J 49/04; Y10S 435/973
   See application file for complete search history.

(56) References Cited

U.S. PATENT DOCUMENTS

| | | |
|---|---|---|
| 4,077,845 A | 3/1978 | Johnson |
| 4,279,862 A | 7/1981 | Bretaudiere et al. |
| 4,318,994 A | 3/1982 | Meyer et al. |
| 4,465,935 A | 8/1984 | von Criegern et al. |
| 4,533,629 A | 8/1985 | Litman et al. |
| 4,537,861 A | 8/1985 | Elings et al. |
| 4,676,274 A | 6/1987 | Brown |
| 4,762,683 A | 8/1988 | Romanauskas |
| 4,858,623 A | 8/1989 | Bradshaw et al. |
| 4,868,130 A | 9/1989 | Hargreaves |
| 4,879,458 A | 11/1989 | Brunfeldt et al. |
| 4,917,865 A | 4/1990 | Romanauskas |
| 5,115,131 A | 5/1992 | Jorgenson et al. |
| 5,122,284 A | 6/1992 | Braynin et al. |
| 5,160,702 A | 11/1992 | Kopf-Sill et al. |
| 5,197,185 A | 3/1993 | McCoy et al. |
| 5,270,166 A | 12/1993 | Parsons et al. |
| 5,310,523 A | 5/1994 | Smethers et al. |
| 5,376,252 A | 12/1994 | Ekstrom et al. |
| 5,472,603 A | 12/1995 | Schembri |
| 5,585,241 A | 12/1996 | Lindmo |
| 5,587,128 A | 12/1996 | Wilding et al. |
| 5,587,293 A | 12/1996 | Kauvar et al. |
| 5,593,838 A | 1/1997 | Zanzucchi et al. |
| 5,608,519 A | 3/1997 | Gourley et al. |
| 5,627,041 A | 5/1997 | Shartle |
| 5,635,358 A | 6/1997 | Wilding et al. |
| 5,637,469 A | 6/1997 | Wilding et al. |
| 5,653,939 A | 8/1997 | Hollis et al. |
| 5,698,162 A | 12/1997 | Belly et al. |
| 5,705,813 A | 1/1998 | Apffel et al. |
| 5,716,825 A | 2/1998 | Hancock et al. |
| 5,773,488 A | 6/1998 | Allmer |
| 5,798,215 A | 8/1998 | Cathey et al. |
| 5,866,345 A | 2/1999 | Wilding et al. |
| 5,869,830 A | 2/1999 | Franzen et al. |
| 5,872,010 A | 2/1999 | Karger et al. |
| 5,905,258 A | 5/1999 | Clemmer et al. |
| 5,912,134 A | 6/1999 | Shartle |
| 5,962,081 A | 10/1999 | Ohman et al. |
| 5,969,353 A | 10/1999 | Hsieh |
| 5,992,820 A | 11/1999 | Fare et al. |
| 5,995,209 A | 11/1999 | Ohman et al. |
| 6,001,307 A | 12/1999 | Naka et al. |
| 6,030,581 A * | 2/2000 | Virtanen ............... B01L 3/5027 369/275.1 |
| 6,046,056 A | 4/2000 | Parce et al. |
| 6,063,589 A | 5/2000 | Kellogg et al. |
| 6,074,827 A | 6/2000 | Nelson et al. |
| 6,110,343 A | 8/2000 | Ramsey et al. |
| 6,113,768 A | 9/2000 | Fuhr et al. |
| 6,126,765 A | 10/2000 | Ohman |
| 6,130,098 A | 10/2000 | Handique et al. |
| 6,132,582 A | 10/2000 | King et al. |
| 6,143,247 A | 11/2000 | Sheppard, Jr. et al. |
| 6,143,248 A | 11/2000 | Kellogg et al. |
| 6,144,447 A | 11/2000 | Ohman et al. |
| 6,191,418 B1 | 2/2001 | Hindsgaul et al. |
| 6,192,768 B1 | 2/2001 | Wallman et al. |
| 6,203,291 B1 | 3/2001 | Stemme et al. |
| 6,221,677 B1 | 4/2001 | Wu et al. |
| 6,271,040 B1 | 8/2001 | Buechler |
| 6,294,392 B1 | 9/2001 | Kuhr et al. |
| 6,296,020 B1 | 10/2001 | McNeely et al. |
| 6,302,134 B1 | 10/2001 | Kellogg et al. |
| 6,319,468 B1 | 11/2001 | Sheppard, Jr. et al. |
| 6,319,469 B1 | 11/2001 | Mian et al. |
| 6,322,682 B1 | 11/2001 | Arvidsson et al. |
| 6,326,083 B1 | 12/2001 | Yang et al. |
| 6,379,929 B1 | 4/2002 | Burns et al. |
| 6,408,878 B2 | 6/2002 | Unger et al. |
| 6,418,968 B1 | 7/2002 | Pezzuto et al. |
| 6,444,461 B1 | 9/2002 | Knapp et al. |
| 6,454,970 B1 | 9/2002 | Ohman et al. |
| 6,459,080 B1 | 10/2002 | Yin et al. |
| 6,481,453 B1 | 11/2002 | O'Connor et al. |
| 6,499,499 B2 | 12/2002 | Dantsker et al. |
| 6,521,182 B1 | 2/2003 | Shartle et al. |
| 6,561,208 B1 | 5/2003 | O'Connor et al. |
| 6,589,729 B2 | 7/2003 | Chan et al. |
| 6,591,852 B1 | 7/2003 | McNeely et al. |
| 6,620,478 B1 | 9/2003 | Ohman |
| 6,632,399 B1 | 10/2003 | Kellogg et al. |
| 6,632,656 B1 | 10/2003 | Thomas et al. |
| 6,637,463 B1 | 10/2003 | Lei et al. |
| 6,653,625 B2 | 11/2003 | Andersson et al. |
| 6,709,869 B2 | 3/2004 | Mian et al. |
| 6,717,136 B2 | 4/2004 | Andersson et al. |
| 6,728,644 B2 | 4/2004 | Bielik et al. |
| 6,737,026 B1 | 5/2004 | Bergh et al. |

(56) References Cited

U.S. PATENT DOCUMENTS

| | | |
|---|---|---|
| 6,811,736 B1 | 11/2004 | Ohman et al. |
| 6,812,456 B2 | 11/2004 | Andersson et al. |
| 6,812,457 B2 | 11/2004 | Andersson et al. |
| 6,852,851 B1 | 2/2005 | Kenrick et al. |
| 6,884,370 B2 | 4/2005 | Ohman et al. |
| 6,884,395 B2 | 4/2005 | Tooke et al. |
| 6,885,230 B2 | 4/2005 | Mehalel |
| 6,908,593 B1 | 6/2005 | Shartle |
| 6,919,058 B2 | 7/2005 | Andersson et al. |
| 6,955,738 B2 | 10/2005 | Derand et al. |
| 6,967,101 B1 | 11/2005 | Larsson et al. |
| 6,992,181 B2 | 1/2006 | Tooke et al. |
| 6,992,278 B2 | 1/2006 | Sjoberg et al. |
| 7,104,517 B1 | 9/2006 | Derand et al. |
| 7,146,056 B2 | 12/2006 | Klein Gunnewiek et al. |
| 7,148,476 B2 | 12/2006 | Andersson et al. |
| 7,169,360 B2 | 1/2007 | Ågren et al. |
| 7,189,368 B2 | 3/2007 | Andersson et al. |
| 7,213,339 B2 | 5/2007 | Ohman et al. |
| 7,221,783 B2 | 5/2007 | Soderman |
| 7,238,255 B2 | 7/2007 | Derand et al. |
| 7,244,398 B2 | 7/2007 | Kotary et al. |
| 7,261,858 B2 | 8/2007 | Agren et al. |
| 7,261,859 B2 | 8/2007 | Andersson et al. |
| 7,275,858 B2 | 10/2007 | Andersson et al. |
| 7,285,255 B2 | 10/2007 | Kadlec et al. |
| 7,295,320 B2 | 11/2007 | Ostlin et al. |
| 7,300,199 B2 | 11/2007 | Andersson et al. |
| 7,323,345 B1 | 1/2008 | Stjernstrom |
| 7,429,354 B2 | 9/2008 | Andersson et al. |
| 7,459,129 B2 | 12/2008 | Andersson et al. |
| 7,553,393 B2 | 6/2009 | Derand et al. |
| 7,759,067 B2 | 7/2010 | Andersson et al. |
| 7,776,272 B2 | 8/2010 | Ekstrand et al. |
| 7,955,575 B2 | 6/2011 | Derand et al. |
| 8,198,505 B2 | 6/2012 | Hird et al. |
| 8,592,219 B2 | 11/2013 | Kange et al. |
| 2001/0055812 A1 | 12/2001 | Mian et al. |
| 2002/0025944 A1 | 2/2002 | Bush et al. |
| 2002/0036018 A1* | 3/2002 | McNeely ............. B01F 5/0403 137/806 |
| 2002/0058273 A1 | 5/2002 | Shipwash |
| 2002/0058329 A1 | 5/2002 | Singh et al. |
| 2002/0076354 A1 | 6/2002 | Cohen |
| 2002/0118355 A1 | 8/2002 | Worthington et al. |
| 2002/0150512 A1 | 10/2002 | Kellogg et al. |
| 2003/0054563 A1 | 3/2003 | Ljungstrom |
| 2003/0066957 A1 | 4/2003 | Andersson et al. |
| 2003/0066959 A1 | 4/2003 | Andersson et al. |
| 2003/0094502 A1 | 5/2003 | Andersson |
| 2003/0173650 A1 | 9/2003 | Larsson et al. |
| 2003/0211012 A1 | 11/2003 | Bergstrom |
| 2003/0225362 A1 | 12/2003 | Currie et al. |
| 2004/0005634 A1 | 1/2004 | Patz et al. |
| 2004/0058408 A1 | 3/2004 | Thomas |
| 2004/0096867 A1 | 5/2004 | Andersson et al. |
| 2004/0099310 A1 | 5/2004 | Andersson |
| 2004/0109793 A1 | 6/2004 | McNeely et al. |
| 2004/0202579 A1 | 10/2004 | Larsson et al. |
| 2005/0042770 A1 | 2/2005 | Derand et al. |
| 2005/0069913 A1 | 3/2005 | Mian et al. |
| 2005/0150459 A1 | 7/2005 | Shang et al. |
| 2005/0153434 A1 | 7/2005 | Andersson et al. |
| 2005/0214442 A1 | 9/2005 | Larsson et al. |
| 2005/0277195 A1 | 12/2005 | Holmquist et al. |

FOREIGN PATENT DOCUMENTS

| | | |
|---|---|---|
| EP | 0282840 A2 | 9/1988 |
| EP | 0073513 B2 | 2/1992 |
| EP | 0241140 B1 | 2/1992 |
| EP | 0655618 A2 | 5/1995 |
| EP | 0745856 A2 | 12/1996 |
| EP | 0977032 A1 | 2/2000 |
| JP | 07-333229 | 12/1995 |
| JP | H11204260A A | 7/1999 |
| WO | 9116966 A1 | 11/1991 |
| WO | 9322053 A1 | 11/1993 |
| WO | 9322054 A1 | 11/1993 |
| WO | 9322055 A2 | 11/1993 |
| WO | 9322058 A1 | 11/1993 |
| WO | 9506870 A1 | 3/1995 |
| WO | 9533986 A1 | 12/1995 |
| WO | 9606354 A1 | 2/1996 |
| WO | 9607919 A1 | 3/1996 |
| WO | 9614933 A1 | 5/1996 |
| WO | 9615450 A1 | 5/1996 |
| WO | 9615576 A1 | 5/1996 |
| WO | 9704297 A1 | 2/1997 |
| WO | 9721090 A1 | 6/1997 |
| WO | 9745730 A1 | 12/1997 |
| WO | 9800231 A1 | 1/1998 |
| WO | 9800709 A1 | 1/1998 |
| WO | 9807019 A1 | 2/1998 |
| WO | 9815356 A1 | 4/1998 |
| WO | 9822625 A1 | 5/1998 |
| WO | 9838510 A2 | 9/1998 |
| WO | 9839645 A1 | 9/1998 |
| WO | 9853311 A2 | 11/1998 |
| WO | WO-9853311 A2 * | 11/1998 ......... B01F 13/0059 |
| WO | 9917093 A1 | 4/1999 |
| WO | 9931275 A1 | 6/1999 |
| WO | 9940174 A1 | 8/1999 |
| WO | 9955827 A1 | 11/1999 |
| WO | 9958245 A1 | 11/1999 |
| WO | 9964160 A1 | 12/1999 |
| WO | 0025921 A1 | 5/2000 |
| WO | 0030167 A1 | 5/2000 |
| WO | 0040750 A1 | 7/2000 |
| WO | 0050172 A1 | 8/2000 |
| WO | 0056808 A2 | 9/2000 |
| WO | 0062042 A1 | 10/2000 |
| WO | 0062931 A1 | 10/2000 |
| WO | 0067293 A1 | 11/2000 |
| WO | 0075312 A1 | 12/2000 |
| WO | 0113126 A1 | 2/2001 |
| WO | 0134302 A2 | 5/2001 |
| WO | 0138865 A1 | 5/2001 |
| WO | 0146465 A2 | 6/2001 |
| WO | 0147637 A1 | 7/2001 |
| WO | 0147638 A2 | 7/2001 |
| WO | 0154810 A1 | 8/2001 |
| WO | 0163241 A2 | 8/2001 |
| WO | 0185602 A1 | 11/2001 |
| WO | 0187486 A2 | 11/2001 |
| WO | 0187487 A2 | 11/2001 |
| WO | 0224652 A1 | 3/2002 |
| WO | 0241997 A1 | 5/2002 |
| WO | 0241998 A1 | 5/2002 |
| WO | 0274438 A2 | 9/2002 |
| WO | 0275312 A1 | 9/2002 |
| WO | 0275775 A1 | 9/2002 |
| WO | 0275776 A1 | 9/2002 |
| WO | 0318198 A1 | 3/2003 |
| WO | 0532999 A1 | 4/2005 |

OTHER PUBLICATIONS

Ekstrand et al., "Microfluidics in a Rotating CD" presented at MICROTAS 2000, Enschede, The Netherlands, May 14-18, 2000.

Sanders et al., "Chip-based microsystems for genomic and proteomic analysis", Trends In Analytical Chemistry, No. 19, 2000, pp. 364-378.

Sato et al., "Determination of Carcinoembryonic Antigen in Human Sera by Integrated Bead-Bed Immunoasay in a Microchip for Cancer Diagnosis", Analytical Chemistry, No. 73, 2001, pp. 1213-1218.

Sato et al.; Integration of an Immunosorbent Assay System: Analysis of Secretory Human Immunoglobulin A on Polystyrene Beads in a Microchip; Anal. Chem. 72:1144-1147, 2000.

Tooke et al, "High-Throughput SNP Scoring in a disposable Micro-Fabricated CD Device Combined with Solid-Phase Pyrosequenc-

(56) References Cited

OTHER PUBLICATIONS ing," Human Genome Meeting, HGM 2000, Vancouver, Canada, Apr. 9-12, 2000.
Tooke et al.; High-throughput SNP scoring in a microfabricated CD device; Amersham Pharmacia Biotech, Uppsala, Sweden.
Zhang et al., Microfabricated Devices for Capillary Electrophoresis-Electrospray Mass Spectrometry; Analytical Chemistry, vol. 71, No. 15, Aug. 1, 1999, pp. 3258-3264.
Eckersten et al., High-Throughput SNP Scoring il1 a Disposable Microfabricated CD Device; presented at HGM 2000, Vancouver, Canada, Apr. 9-12, 2000.
Gustafsson et al., "Integrated Sample Preparation and Detection on a Microfluidic Compact Disk (CD) Decreases Detection Limits for Protein Identification by Mass Spectrometry," Proceedings of the 49th ASMS Conference on Mass Spectometry and Allied Topics, Chicago, Illinois, May 27-31, 2001.

\* cited by examiner

CHARACTERIZATION OF REACTION VARIABLES

The present application is a continuation application of U.S. patent application Ser. No. 12/794,915, filed Jun. 7, 2010, which is a continuation application of U.S. patent application Ser. No. 10/472,421, filed Sep. 19, 2003, which was the National Stage Application under 35 USC 371 of International Application No. PCT/SE02/00537 filed Mar. 19, 2002, which application Ser. No. 10/472,421 is also a continuation in part of U.S. application Ser. No. 09/811,741, filed Mar. 19, 2001 and which application Ser. No. 10/472,421 is a continuation in part of U.S. application Ser. No. 09/812,123, filed Mar. 19, 2001 and this application claims priority to U.S. Provisional Application Serial No. 60/322,621, filed Sep. 17, 2001 and claims priority to Swedish Application Serial No. 0100951-3 filed Mar. 19, 2001 and claims priority to Swedish Application Serial No. 0100952-1, filed Mar. 19, 2001 and claims priority to Swedish Application Serial No. 0103117-8, filed Sep. 17, 2001 and claims priority to Swedish Application Serial No. 0200242-6, filed Jan. 28, 2002, all of which applications are incorporated by reference herein in their entirety.

TECHNICAL FIELD

The present invention relates to a microscale method for the characterization of at least one reaction variable that influence the formation or dissociation of an affinity complex comprising a ligand and a binder. The ligand and the binder have affinity to each other and are affinity counterparts.

BACKGROUND TECHNOLOGY

Microscale methods have previously been used for finding new combinations of ligands and binders for screening libraries of compounds for
(a) new drug candidates which are based on a receptor-ligand interaction, and
(b) new ligand candidates for affinity assays, affinity chromatography etc. Microscale methods have also been suggested for optimizing the conditions for formation or dissociation of a particular affinity complex or when selecting affinity counterparts for other reasons.

Microscale methods have also been used for determining the amount of a particular compound (analyte) in a sample.

Methods have been used that are based on affinity capture of a binder or an analyte by an affinity counterpart that is immobilized or immobilizable to a solid phase.

Typically the formation of the complex on a solid phase has been performed under non-flow-conditions. See for instance Eteshola et al, Sensors and Actuators B 72 (2001) 129-133; Sato et al, Anal. Chem. 72 (2000) 1144-1147; and WO 9721090 (camera, Mian et al).

Non-flow conditions will simplify the methods but information that only can be obtained from experiments performed under flow conditions will be missed. For small molecules non-flow conditions may be acceptable because their diffusion rates are often relatively high and orientation of their binding sites for binding is uncomplicated. This is normally not applicable to larger molecules. Without controlling the liquid flow accurate information will be difficult to obtain for large molecules.

Recently a MALDI MS integrated microfluidic affinity system based on affinity binding to a reverse phase matrix has been presented. In this system a protein digest was adsorbed to a reverse phase matrix and subsequently desorbed and transported to an outlet port that functioned as a MALDI MS target. (Integrated sample preparation and MALDI MS on a microfluidic compact disc (CD with improved sensitivity) (Magnus Gustavsson et al) ASMS 2001. The demand on the reproducibility in the binding, the control of the liquid flow rate, and the residence time was low.

WO 0138865 (Univ. of Alberta, Harrison et al) describes a solid phase extraction method in a singular microchannel structure utilizing flow conditions and affinity binding. In another example the publication shows saturation of solid phase bound anti-theopyhilline antibodies with theophylline.

Definitions

Reaction variables are mainly of two kinds: 1) variables related to affinity reactants with the subgroups a) amounts including presence and/or absence, and b) properties of affinity reactants including affinity, and 2) reaction conditions.

Group 1a comprises amounts in mass units, molar units, relative amounts, concentrations, activity/mass unit, activity/volume unit, relative activities etc. Activity refers to (i) biological activity, (ii) binding activity for an affinity counterpart etc. Biological activity includes enzyme activity binding activity towards a native or synthetic affinity counterpart, cell activity etc.

Group 1b comprises properties of an affinity reactant (a ligand and/or a binder).

Typically this group comprises properties of inhibitors and promotors for the formation or dissociation of an affinity complex, enzymes, substrates, cofactors, cosubstrates, coenzymes, receptors, hormones, antibodies and antigen/hapten-binding fragments thereof, antigens/haptens etc. Synthetic and recombinant forms are included.

If a variable of group 1b varies or are different between samples, microchannel structures, reaction microcavities, aliquots of liquid etc this primarily means that different molecular entities are present in respective unit.

The properties related to group 1b comprises affinity which includes affinity constants (and the corresponding constant for the dissociation), rates for formation and dissociation, knowledge about counterpart(s) towards which a binder has/have affinity and vice versa (specificity, selectivity etc) etc. Affinity also comprises relative affinity of different complexes, for instance a common ligand versus a range of binders and vice versa, a common complex versus changes in reaction conditions etc.

Reaction conditions in this context means reaction variables that are not related to a property of an affinity reactant. Reaction conditions comprise pH, temperature, ionic strength (including type of salts), hydrogen bond breaking agents (denaturing agents, amount and kind)), detergents (amount and kind), liquid flow, immobilization techniques, solid phases etc.

Affinity reactants (ligands and binders) that are to be characterized with respect to group 1 variables are called "analytes". The term "Analyte" also includes analyte-derived entities that originate from an original analyte in an original sample that has been processed to the sample used in the microfluidic device for step (ii). This preprocessing may take place outside the microfluidic device and/or in separate substructures within the microfluidic device. The amount of an analyte-derived entity in a processed sample is a function of the occurrence of the original analyte in the original sample.

The term "analogues" is used for two or more binders or ligands that are capable of inhibiting or competing with each other for affinity binding to a common affinity counterpart. In the same manner "analogue" is also used for an analyte.

A microfluidic device comprises at least one microchannel structure through which liquid flow is used for the transport of reactants The terms "microformat", "microchannel" etc contemplate that a microchannel structure comprises one or more cavities and/or channels that have a depth and/or a width that is $\leq 10^3$ µm, preferably $\leq 10^2$ µm. The volumes of microcavities/microchambers are typically $\leq 1000$ nl (=nl-range), such as $\leq 500$ nl or $\leq 5100$ nl or $\leq 50$ nl, but may also be larger, i.e. in the interval 1-1000 µl, such as 1-100 µl or 1-10 µl.

The term "microfluidic method" means that (a) the method is performed in a microfluidic device, and (b) the liquid volumes are in the microformat.

A "library" is a set of two, three, four or more compounds or substances, for instance $\geq 10$, such as $\geq 100$ or $\geq 1000$ or $\geq 10000$. Typical examples are recombinant, synthetic or native sets of nucleotides, oligonucleotides, polynucleotides, amino acids, oligopeptides, polypeptides, proteins, lipids, other organic and inorganic compounds, carbohydrates, bacteria, phages, polymers, biopolymers etc. Each individual library may contain members of different classes, for instance polypeptides and polynucleotides, carbohydrates and proteins etc. A library may also include sets that are derived from nature, e.g. sets of native proteins in which the individual proteins relates to each other due to post-translational modifications, isoproteins such as isoenzymes etc. Examples of post-translational modifications that can result in a library are phosphorylation, activating cleavage, glycosylation, ubiquitination, etc.

The term "library" also includes sets of other reaction variables, such as different pH values, different immobilization groups, different ionic strengths, different concentrations, different salts, different solid phases, different spacers etc.

The "library" also includes a collection of samples (aliquots of liquid) differing with respect to at least one reaction variables.

OBJECTS OF THE INVENTION

A first object is to provide an improved microscale method for quantifying the amount of an analyte in a plurality of samples by using assay methods that are based on specific affinity binding and capture to a solid phase A second objective is to provide a fluidic function that when incorporated into the microchannel structures of a microfluidic device will standardize the flow rate in the individual microchannel structures in a microfluidic device, i.e. to control the flow rate such that the inter-channel variation is reduced to an acceptable level.

A third objective of the present invention is to provide a robust microfluidic system and method that can be used for parallel screening of reaction variables in order to find new and optimal binder-ligand combinations and/or to grade affinity for a range of affinity complexes, ligands and binders, and/or to optimize processes involving formation or dissociation of immobilized affinity complexes under flow conditions.

These objects primarily concern methods which utilize interactions involving at least one affinity reactant which is relatively large and/or comprises one or more functional groups comprising a heteroatom selected amongst nitrogen, oxygen, sulphur and phosphorous. Relatively large in this context means that the affinity reactant simultaneously can bind two affinity counterparts and/or has a molecular weight $\geq 1000$ dalton, such as $\geq 2000$ or $\geq 10000$ dalton. Typically one of the affinity reactants is polymeric, such as a biopolymer comprising carbohydrate structure and/or peptide structure and/or nucleotide structure and/or lipid structure. Molecules that are not large are considered to be small.

BRIEF DESCRIPTION OF THE DRAWINGS

FIGS. 1a and 1b are identical except that FIG. 1a gives the dimensions and FIG. 1b hydrophobic surface breaks and their dimensions.

Figure 1A:
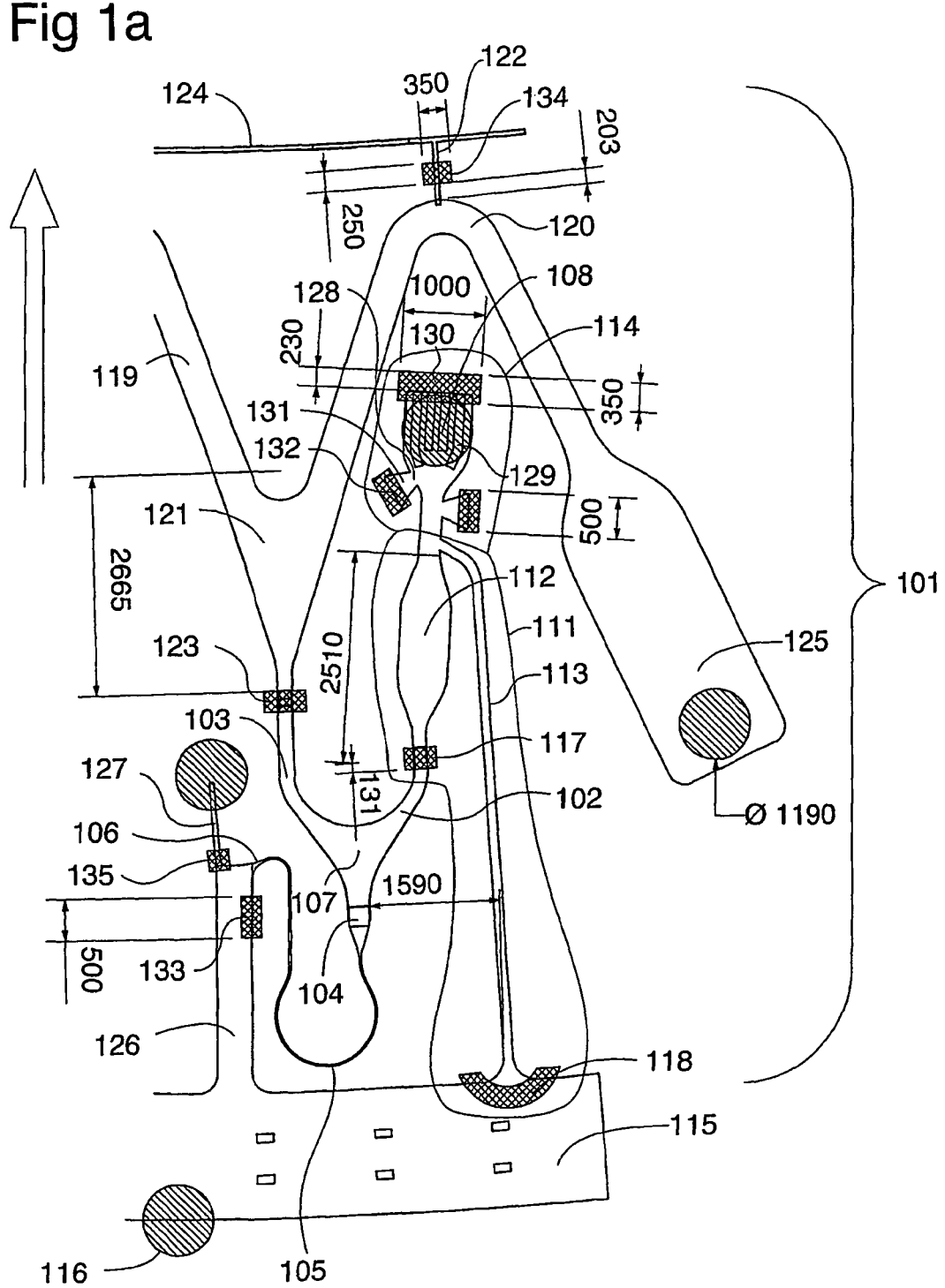
FIGS. 1a and 1b illustrate a variant of a preferred microchannel structure that has a narrow microconduit that create a significant pressure drop. This variant has been used for the model study presented in the experimental part.
Figure 1B:
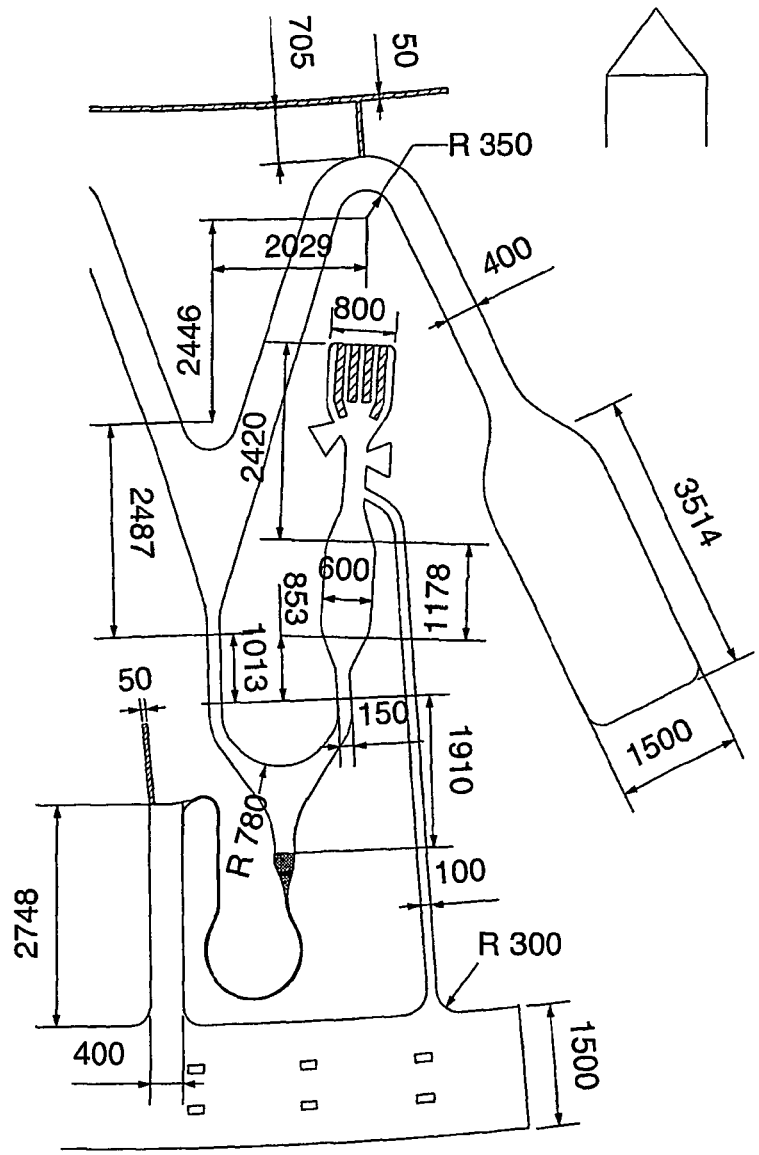
Figure 2:
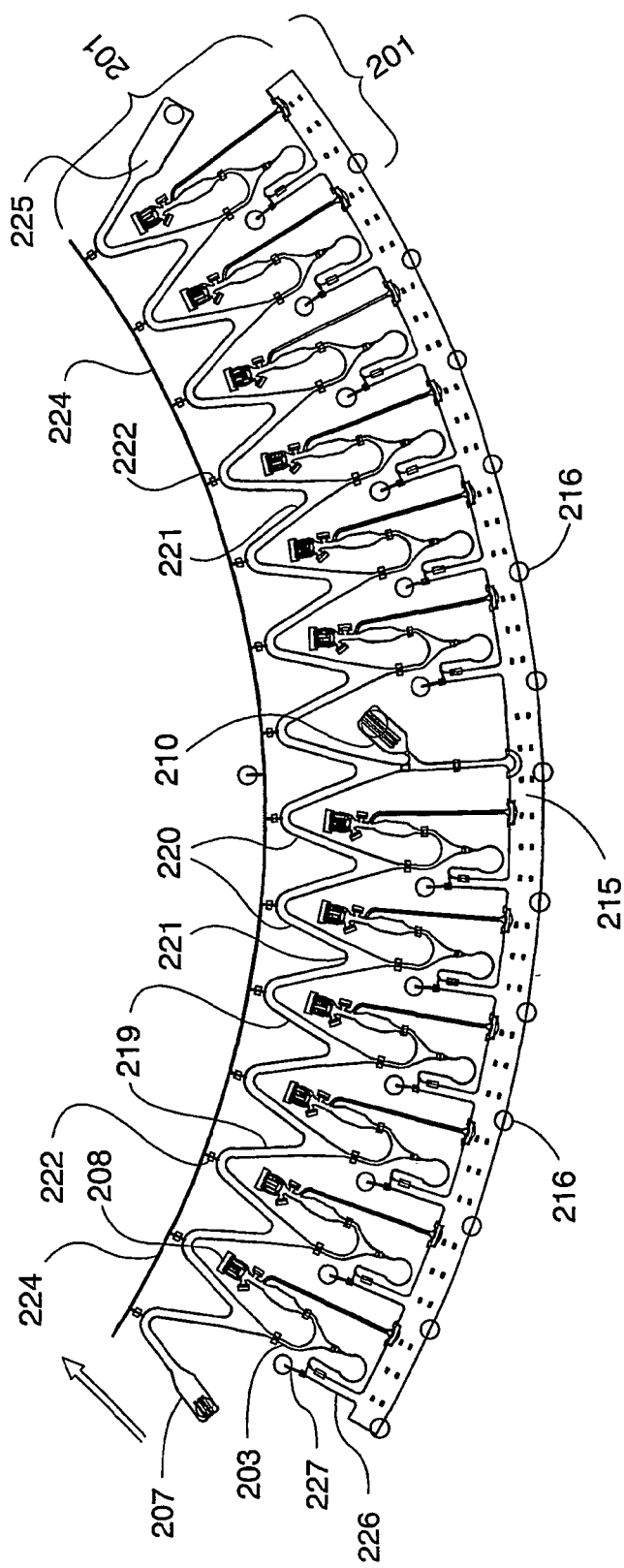
FIG. 2 illustrates a set of microchannel structures of the same kind as used in the experimental part. The structures are linked together by a common distribution channel and a common waste channel.

The structures shown in FIGS. 1-2 are intended to be placed on a circular disc around its axis of symmetry (spinning axis). The arrow shows the direction towards the center of the disc. Note also the arc-like configuration.

SUMMARY OF THE INVENTION

The present inventors have recognized that the method defined under "Technical Field" above can be improved by
(a) utilizing a microfluidic device comprising two or more microchannel structures in which the flow is under a common flow control, and
(b) performing formation of the affinity complex under flow conditions in at least two of the microchannel structures and retaining an immobilized form of the formed affinity complex under flow conditions in a reaction microcavity in each of the microchannel structures used.

In a similar manner the principle of common flow control and flow conditions are applied to the dissociation of an affinity complex retained in the reaction microcavity for the characterization of reaction variables influencing the dissociation reaction.

The inventors have also recognized a number of additional features that can reduce the effects of variations in flow between different microchannel structures within the same device (inter-channel variation):
(a) A means for flow restriction downstream the reaction microcavity in each microchannel structure for creating a significant pressure drop.
(b) A porous matrix placed in a desired part, for instance the reaction microcavity or immediately downstream the reaction microcavity, of each microchannel structure for creating a significant pressure drop.
(c) A packed bed of monosized particles instead of polysized particles in the reaction microcavity.
(d) a pulse giving increased flow will assist in over-coming inter-channel variations in flow resistance, in particular when initiating flow and/or when the liquid is to pass through branchings and curvatures.
(e) Anti-wicking means in inner edges downstream and in close proximity to the outlet end of the outlet microconduit which leads waste liquids from a reaction microcavity.
(f) Excess of solid phase affinity reactant (e.g. binder (immobilized reactant)) in the reaction microcavity.
(g) Selecting flow rates that accomplish residence times ≥0.010 seconds for the formation of complex in the reaction microcavity.

Significant pressure drop is relative to inter-channel variations in flow resistance.

DETAILED DESCRIPTION OF THE INVENTION

The invention is a microscale method for characterizing at least one reaction variable. The method is generally defined in the first paragraph. The characterizing feature comprises four steps:

Step (i): Providing a microfluidic device comprising a plurality of microchannel structures that are under common flow control. Each of the structures comprises a reaction microcavity for retaining an affinity complex.

Step (ii): Performing essentially in parallel an experiment in each of two or more of the plurality of microchannel structures. Each experiment comprises:
 (a) forming an immobilized form of the complex and retaining under flow conditions this form within the reaction microcavity, or
 (b) dissociating an immobilized form of the complex within the reaction microcavity.

The reaction variables referred to are different and/or are uncharacterized for two or more of the experiments. Other reaction variables are kept essentially constant. Dissociating is typically performed under flow conditions. The immobilized form in (b) is introduced prior to step (ii). The formation of the retained complex is a function of the introduction of the ligand and the binder.

Step (iii): Measuring the presentation of the complex in the reaction microcavity in each of said two or more microchannel structures.

Step (iv): Characterizing said at least one reaction variable based on the values for presentation which is measured in step (iii).

The experiments are initiated by introducing the appropriate liquid aliquots into inlet ports of the device and applying the appropriate driving force for liquid flow.

In the same microfluidic device there may also be run other similar or dissimilar experiments in parallel with those defined above.

The term "essentially constant" in this context means that the other variables are kept within ranges where the outcome of the experiments will be essentially the same.

In the preferred variants, the reaction microcavities to be used in the method and provided in step (i) comprise an affinity reactant (affinity binder) that in step (ii) will be incorporated into the immobilized complex.

Common Flow Control and Liquid Flow Conditions for Step (Steps (i) and (ii)).

The term "common flow control" means that when a driving force for a liquid flow is applied in one part of a microchannel structure (structure 1), there will also be applied a driving force for liquid flow in the corresponding part of each of the other microchannel structures of the device. The driving force in the individual channels derives from the same source, e.g. spinning the device if centrifugal force is the driving force. Moreover, an increase or a decrease in driving force in one microchannel structure is paralleled with an increase or a decrease in the other microchannel structures. The size of the force (and the liquid flow rate) may differ between different microchannel structures for which common flow control is applied. In centrifugal based systems, for instance, the designs of the microchannel structures may differ and/or the microchannel structures may be placed at different radial distances.

Common flow control primarily refers to the flow through the reaction microcavity (solid phase) when the immobilized complex is formed and retained. Flow control may be less critical in other parts of the structures and/or for other steps of the method.

The liquid flow may be driven by distinct means that either is present in or external to the device. Thus, liquid flow may be created by electroosmosis, micropumps, expanding gas etc. Another alternative is to use forces such as capillary force and inertia force including gravitational force and centrifugal force to drive the liquid, i.e. forces which do not require any means on the microfluidic device.

The appropriate flow rate through the reaction microcavity (step (ii)) depends on a number of factors, such as the affinity pair used for forming the immobilized complex, the volume of the reaction microcavity, the solid phase in the microcavity etc. Typically the flow rate should give a residence time of ≥0.010 seconds such as ≥0.050 sec or ≥0.1 sec with an upper limit that typically is below 2 hours such as below 1 hour. Illustrative flow rates are within 0.01-100 nl/sec, typically 0.1-10 nl/sec. Residence time refers to the time it takes for a liquid aliquot to pass through the reaction microcavity (i.e. through the solid phase).

An acceptable flow control depends on a particular application including concentrations of reactants, their diffusion properties and reaction rates, etc. Sufficient flow control in most cases means that the inter-channel variation for residence time is within the mean residence time +90%, such as +75% or +50% or +25%.

According to a preferred variant of the invention, common flow control is accomplished by spinning a microfluidic device in which the microchannel structures are oriented from an inward position to an outward position in relation to an axis of symmetry of a substrate and utilizing the centrifugal force for driving the liquid. Common flow control also include that centrifugal force is used to create a sufficient local hydrostatic pressure within a structure to drive a liquid aliquot through an outward (downward) and/or an inward (upward) bent of a microchannel structure. See for instance WO 0146465 (Gyros AB).

Typical spinning speeds are within the interval 50-25000 rpm, such as 50-15000 rpm. The spinning speed within a given protocol may vary, for instance comprise sequences with individual ramps of acceleration, deceleration, and constant spinning. It may be beneficial to include a pulse of increased spinning at certain positions. See above.

Microfluidic Device (Step (i)).

The present invention is primarily intended for geometric arrangements in which the microchannel structures are present in a substrate (microfluidic device) that has an axis of symmetry. Each microchannel structure is then oriented in an outward direction relative to the axis of symmetry, i.e.
(a) the reaction microcavity is part of a substructure which also comprises a structural unit delivering liquid to the reaction microcavity, and (b) the latter unit is at a shorter radial distance than the reaction microcavity and communicates with an inlet port.

An inlet port is typically located at a shorter radial distance than the reaction microcavity. Downstream the reaction microcavity there may be an outlet port, typically located at a larger radial distance than the reaction microcavity. By utilizing capillary force and/or other non-centrifugal forces for the introduction of a liquid into a microchannel structure, inlet ports may be located at in principle any radial distance, e.g. more remote from the axis of symmetry than an outlet port and/or the reaction microcavity.

The microchannel structures may or may not be oriented in a plane perpendicular to the axis of symmetry.

In centrifugal based systems a "higher" or an "upper" level/position will be at a shorter radial distance (inner position) compared to a "lower" level/position (outer position). Similarly, the terms "up", "upward", "inwards", and "down", "downwards", "outwards" etc will mean towards and from, respectively, the spinning axis. This applies if not otherwise is specified. With respect to other arrangement/substrates and conventional driving forces, i.e. gravity force, externally applied pressure, electro-osmotically driven flows etc, these terms have their conventional meaning.

Axes of symmetry are n-numbered ($C_n$) where n is an integer between 2 and ∞, preferably 6, 7, 8 and larger, for instance ∞. In preferred cases the substrate (microfluidic device) as such may have a circular, cylindrical, spherical or conical symmetry ($C_\infty$).

The preferred devices are typically disc-shaped with sizes and forms similar to the conventional CD-format, e.g. in the interval from 10% up to 300% of the conventional CD-radii.

Suitable microfluidic devices may be manufactured from a planar substrate surface comprising a plurality of uncovered microchannel structures that in a subsequent step are covered by another planar substrate (lid). See WO 9116966 (Pharmacia Biotech AB) and WO 0154810 (Gyros AB). At least one of the substrates may be transparent, e.g. the second substrate (lid). Both substrates are preferably fabricated from plastic material, e.g. plastic polymeric material.

Different applications require different surface characteristics. This means that in the case aqueous liquids are to be transported within the microchannel structures hydrophilization may be required. See for instance WO 0056808 (Gyros AB) and WO 0147637 (Gyros AB). For aqueous liquids an essential part of the inner surfaces should have water contact angles ≤90°, such as ≤40° or ≤30° or ≤20° at the temperature of use. At least two or three of the inner walls enclosing the channels should comply with this range. Surfaces in passive valves, anti-wicking means etc are excluded from these general rules.

Non-wettable surface breaks may be introduced at predetermined positions in the inner walls of the microchannel structures before covering the uncovered microchannel structures (WO 9958245, Amersham Pharmacia Biotech AB) and WO 0185602, Åmic AB & Gyros AB). For aqueous liquids this means hydrophobic surface breaks. Surface breaks may be used for controlling the liquid flow within the structures, e.g. anti-wicking, passive valves, directing liquids etc. See below. In FIG. 1a, surface breaks are cross-hatched and openings (inlets, outlets, vents) in the covering substrate (lid) are represented by hatched circles.

FIGS. 1a-b and 2 illustrate a microchannel structure (101) that can be used in the present invention. The structure comprises a reaction microcavity (104) connected to one or more inlet microconduits (102 and 103) and an outlet microconduit (105) with an outlet end (106). When the structure is used the immobilized complex becomes retained in the reaction microcavity (104). Alternatively the reaction microcavity contains the affinity complex from the beginning and the method means dissociation of the complex.

If there are two or more inlet microconduits (102 and 103) they typically merge before reaching the reaction microcavity (104). In the case the reaction microcavity contains a solid phase in form of particles the trespass into the outlet microconduit (105) typically is a sharp drop in the cross-sectional area that prevents the particles from passing into the outlet microconduit.

For centrifugal based systems, two inlet microconduits (102 and 103) typically form at downward bent (107) with shanks corresponding to the inlet microconduits (102 and 103). The outlet microconduit (105) is connected to the lower part of the bent via the reaction microcavity (104).

An inlet microconduit (102,103) may be connected to an inlet port (108,208 and 209 and 210) via a functional unit. This unit may be a volume-defining unit (111) that comprises a metering microcavity (112) connected to one of the inlet microconduits (102), an overflow channel (113) that starts in a narrow conduit part between the metering cavity (112) and the inlet unit (114) and ends in a waste function, for instance waste comprising a common waste reservoir/channel (115,215). The waste function may have one or more outlet ports (116216). The volume-defining unit (111) comprises valve functions (117,118) that are associated with the overflow channel (113) and with the outlet end of the metering microcavity (112). For centrifugal based systems these valve functions are typically passive and preferably based on local changes in surface characteristics. The valve function (118) is at a larger radial distance than the valve function (117). This means that the positions of these valves are selected to support that liquid in the overflow channel (113) is passed into the waste function at a lower spinning speed than liquid in the metering microcavity (112) is passed into the inlet microconduit (102). A volume-defining unit of this kind (111) is primarily intended for liquid aliquots that are to be introduced with high accuracy with respect to volume. This means liquid aliquots that contain (a) an analyte and/or
(b) a reaction variables of group 2 that varies between microchannel structures and/or
(c) any other reagent that has to be delivered with a high accuracy.

Aliquots of type (a) and (b) will be called aliquot 1.

An alternative functional unit connected to one of the inlet microconduits (102,103) is a unit for distributing liquid aliquots to separate microchannel structures. The unit may be in the form of a distribution channel (119,219) that is common for several microchannel structures (101,201). For centrifugal based system the channel may have alternating upper and lower parts (120,220 and 121,221, respectively) with an inlet vent (122,222) to ambient atmosphere in each upper part (120) and liquid communication in each lower part (121) via a valve function (123) to one of the inlet conduits (103,203) of each microchannel structure (101, 201). The vents (122,222) communicate with ambient atmosphere via a common venting channel (124,224). The distribution channel may have one or more inlet ports (209,210) and one or more outlet ports (125,225) (only one shown).

As shown in the figures the outlet end (106) may mouth into a waste conduit chamber (126) (belonging to the microchannel structure). This chamber in turn may mouth into a common waste conduit or a common waste reservoir (115). Although not preferred, the outlet conduit (105) may in an alternative variant mouth directly into a common waste chamber or into ambient atmosphere. For centrifugal based systems utilizing passive valves, the outlet end (106) of the outlet microconduit (105) typically is at the same or a higher level than the reaction micocavity (preferably its top part) (104). According to one inventive aspect of the invention the outlet microconduit (105) possibly in combination with a solid phase in the reaction microcavity (104) are able to produce a pressure drop against a liquid flow passing through the microchannel structure, which is significantly larger that the resistance to flow upstream the reaction microcavity (104). The pressure drop in a microconduit is proportional to its length and inversely proportional to its hydrodynamic cross-sectional area.

In the invention the pressure drop across the outlet microconduit (105) between the reaction microcavity (104) and the waste chamber (126) should be large enough to level out inter-channel differences (variations) in flow resistances that primarily depend on (a) inner surface characteristics upstream the reaction microcavity and (b) the solid phase used (for instance the packing geometry may differ).

The principles outlined have lead to the design of the microchannel structures used in the experimental part (FIGS. 1-2):
(a) Reaction microcavities (104) with a depth of 100 μm and width of 250 μm,
(b) Outlet microconduits (105) with a depth of 10 μm, a width of 20 μm and a length of 4.56 mm.

Other parts of the microchannel structures had a depth of 100 μm.

There may be vents to ambient atmosphere at appropriate positions to
(a) level out over-pressure that may be created in "dead-ends" when liquid is introduced into a microchannel structure, or
(b) interrupt flow at certain positions.

In the variant illustrated in the FIGS. 1-2, the second kind is present in inlet port (108,208). Venting functions (122,222 and 127,227) that break a liquid flow are also present in the common distribution channel and in the waste chamber (119,219 and 126,226, respectively).

The inlet ports (108,208 and 209 and 210) preferably are connected to a microcavity (128), which typically is narrowing inwards the microchannel structure and has longitudinal projections (ridges) (129) in the flow direction. These ridges will facilitate quick transport of a dispensed liquid aliquot into the interior of an inlet unit. The inlet ports also may have a non-wettable area (typically hydrophobised) (130, cross-hatched) that will direct a dispensed liquid into the inlet unit (114).

In order to avoid undesired loss and transport of liquid via wicking, the microchannel structures may be equipped with anti-wicking means at selected positions in form of changes in surface characteristics. The changes are are typically local and may be related to geometric surface characteristics (131) and/or chemical surface characteristics (132,133)(cross-hatched area). See WO 9958245, Amersham Pharmacia Biotech AB) and U.S. Ser. No. 60/315,471 and the corresponding International Patent Application. For aqueous liquids this means that the change is from hydrophilic to hydrophobic. There is also an anti-wicking function (134, 135,123,117) (cross-hatched) present at the inlet vents (127, 122) and in the passive valves (123,117).

Valves are preferably passive, i.e. passage of a liquid will depend on the applied driving force and the physicochemical match between a liquid and the inner surface at the valve position. No movable mechanical parts are needed.

Examples are capillary valves that are based purely on a change in geometric surface characteristics (WO 9615576 (David Samoff Res. Inst.) and WO 9807019 (Gamera). Preferred passive valves are based on a change in chemical surface characteristics, i.e. non-wettable surface breaks. For aqueous liquids this means hydrophobic surface breaks (WO 9958245, Amersham Pharmacia Biotech AB). Valves may also be based on a combination of changes in both chemical and geometric surface characteristics. The changes are typical local. See also U.S. Ser. No. 60/315,471 and the corresponding International Patent Application. Other kinds of valves may also be used.

More details about inlet units, distribution units, volume-defining units, waste conduits, anti-wicking means and valves, in particular for centrifugal based systems, are given in U.S. Ser. No. 60/315,417 and the corresponding International Patent Application.

Reaction Microcavity and Solid Phase.

The geometry of reaction microcavity (104) is preferably a straight microchannel that that may be continuously widening and/or narrowing. At least a part of the wall of the reaction microcavity is transparent with respect to the principle used for measuring the presentation of the complex.

The reaction microcavity preferably comprises a catching affinity reactant immobilized to a solid phase, which is kept within the reaction microcavity.

The solid phase is derivatized with a reactant (capturing reactant) that can be incorporated by affinity into the affinity complex that is formed in immobilized form in step (ii). The capturing reactant may be an immobilized form of the ligand or the binder.

The solid phase may be the surface of the inner wall of the microcavity (104), the inner surface of a porous monolith that wholly or partly will occupy the interior of the reaction microcavity or a population of porous or non-porous particles that are packed to a bed. In the case the solid phase comprises particles there should be retaining means associated with the downstream end of the reaction microcavity. This means is preferably in the form of a constriction, e.g. in the form of a barrier, that prevents the particles from leaving the microcavity. The particle diameter/size should at least be of the same size as or larger than the smallest dimension of the opening in the constricted part. Another kind of retaining means is magnetic particles combined with an externally applied magnetic field.

A porous monolith may be fabricated in one piece of material or may comprise particles that are attached to each other.

By the term "porous particles" is meant that the particles can be penetrated by soluble reactants that are to be incorporated into the affinity complex. This typically means Kav values within the interval of 0.4-0.95 for these reactants. Non-porous particles have a Kav-value below 0.4 with respect to the same reactants. Porous monoliths have pores that are large enough to permit mass transport of the reactants through the matrix by the liquid flow applied.

The particles may be spherical or non-spherical. With respect to non-spherical particles, diameters and sizes refer to the "hydrodynamic" diameters.

The particles are preferably monodisperse (monosized) by which is meant that the population of particles placed in a reaction microcavity has a size distribution with more than 95% of the particles within the range of the mean particle size ±5%. Population of particles that are outside this range are polydisperse (polysized).

The solid phase may or may not be transparent for the principle used for measuring the complex.

The material in the solid phase, e.g. the particles, is typically polymeric, for instance a synthetic polymer or a biopolymer. The term biopolymer includes semi-synthetic polymers comprising a polymer chain derived from a native biopolymer. The particles and other forms of solid phases are typically hydrophilic in the case the liquid flow is aqueous. In this context hydrophilic encompasses that a porous solid phase, e.g. a packed bead, will be penetrated by water. The term also indicates that the surfaces of the particles shall expose a plurality of polar functional groups in which there is a heteroatom selected amongst oxygen, sulphur, and nitrogen. Appropriate functional groups can be selected amongst hydroxy groups, straight eythylene oxide groups ($[-CH_2CH_2O-]_n$, n an integer >0), amino groups, carboxy groups, sulphone groups etc, with preference for those groups that are neutral independent of pH. A hydrophobic particle may be hydrophilized, for instance by introducing hydrophilic groups. See for instance the experimental part. The coating technique is similar to the technique presented in WO 9800709 (Pharmacia Biotech AB, Arvidsson & Ekström).

The techniques for immobilization may be selected amongst those that are commonly known in the field, for instance the bonding to the solid phase may be solely via covalent bonds, affinity bonds (for instance biospecific affinity bonds), physical adsorption (mainly hydrophobic interaction) etc. Examples of biospecific affinity bonds that can be used are bonds between strepavidin and a biotinylated affinity reactant, high affinity antibody and a haptenylated affinity reactant etc.

Other Functional Units in the Microchannel Structures.

A microchannel structure may also comprise separate or combined units that enables:
(1) separation of particulate matter from a liquid aliquot introduced via an inlet port,
(2) mixing, e.g. for the formation of an affinity complex upstream the reaction microcavity, and
(3) detection of (a) a reactant that has passed through the reaction microcavity, or (b) a component released from the complex formed in the reaction microcavity.

Except for unit 3, these functional units if present may be are located upstream the reaction microcavity.

A unit for separation of particulate matter is typically positioned upstream a volume metering unit or the two units are combined in a common unit.

Preferred separation units, volume metering units and mixing units are given in U.S. Ser. No. 60/315,417 and the corresponding International Application.

Additional units may also be present.

The presence of units 1-2 means that the protocol used for step (ii) may include at least one substep selected from
(ii.a) a separation step, and
(ii.b) a mixing step that may include formation of the affinity complex that is retained in immobilized form in the reaction microcavity.

The separation step may be carried out simultaneously with a volume-metering step if each of the microchannel structures used can utilize a combined separation/volume metering unit. Otherwise the separation step is typically upstream a volume-metering step, in particular if the separation step is used to clean a sample. A mixing step, if present, is typically downstream a volume metering step.

A separate detection microcavity may enable measuring of:
an analytically detectable entity that is released from the complex retained in step (ii),
an enzyme product in the case the complex has enzyme activity and a substrate has been passed through the reaction microcavity subsequent to step (ii),
a compound passing through the reaction microcavity as a functional control,
a second analyte by retaining an immobilized form of a complex that is different from the complex retained in step (ii),
a standard compound (calibrator) that is passing through the reaction microcavity without interfering with steps (ii) and (iii).

The first two alternatives may also be part of step (iii).

Protocols Comprising Formation or Dissociation of an Immobilized Complex in the Reaction Microcavity (Step (ii)).

A. Determination of an Uncharacterized Amount of an Analyte.

These protocols are selected amongst biospecific affinity assays that are used for the determination of an analyte in a sample. The principles are well known in the field. The protocols encompass that one or more affinity counterparts to the analyte are used for the formation of an affinity complex which is then measured and related to the amount of the analyte in a sample. The assay conditions are selected such that the amount of the complex becomes a function of the amount of analyte in the sample.

In the variants used in the invention, the complex to be measured corresponds to the immobilized complex retained in a reaction microcavity in step (ii). Depending on the protocol used this complex may or may not comprise the original analyte of the original sample introduced into the microfluidic device. Reaction variables other than the amount of analyte are in principle kept essentially constant for experiments run in different microchannel structures.

Step (ii) may comprise introduction of one or more additional reactants that will become incorporated into the retained complex in order to facilitate its measurement in step (iii). Similarly step (iii) may comprise introduction of one or more additional reactants that might be needed for the measurement of the complex formed in step (ii).

The affinity reactant that defines the link between the solid phase and the immobilized complex to be measured in step (iii) may be introduced by the manufacturer and therefore provided in step (i). Other reactants, including the analyte, are introduced in subsequent steps. This may be done in sequence, in parallel, and/or as mixtures. One or more additional inlet ports may be used. If needed, mixing of affinity reactants and liquids may take place within separate mixing units that are located upstream the reaction microcavity.

According to the invention, amounts can be determined during both diffusion-limiting and non-diffusion-limiting conditions if proper care has been taken. The flow rate may in principle be used to secure that the conditions contemplated are at hand, the general guide-line being that a decrease in flow rate (increase in residence time) will favor non-diffusion limiting conditions and vice versa for diffusion-limiting conditions. These rules primarily apply to large molecules.

Competitive/Inhibition Protocols.

In these protocols the analyte and an analyte analogue are competing with each other for binding to a limiting amount of an affinity counterpart to the analyte. This counterpart may be
(a) immobilized or immobilizable if the analyte analogue is soluble and analytically detectable, and (b) analytically detectable if the analyte analogue is immobilized or immobilizable.

At the filing date variant (b) is of great interest for the invention. This variant includes that the analyte and its affinity counterpart are preincubated before reaching the reaction microcavity, for instance outside the microfluidic device or in a separate mixing microcavity upstream the reaction microcavity. The mixture is transported through the reaction microcavity where the free (=uncomplexed) affinity counterpart forms an affinity complex with an immobilized analyte analogue. This complex is subsequently measured in step (iii).

Competitive variants also include displacement assays in which an immobilized or immobilizable affinity complex comprising two affinity counterparts is incubated with a sample containing an analyte. Provided that one of the affinity counterparts is an analytically detectable analyte analogue, the analyte will displace the analyte analogue in the complex, which also means that the signal from the complex will change.

A preferred displacement assay is to provide this kind of complex in immobilized form in the reaction microcavity in step (i). In step (ii) the analyte will displace the analyte analogue of the immobilized complex. In step (iii) the amount of complex containing the analyte is measured directly in the reaction microcavity or indirectly from released analytically detectable analyte analogue in a separate detection microcavity downstream the reaction microcavity.

Competitive variants are particularly adapted for analytes that have difficulties in binding two or more affinity counterparts simultaneously, i.e. relatively small molecules.

Non-Competitive Protocols

These protocols typically utilize non-limiting amounts of one or more affinity counterparts to the analyte.

The most important non-competitive protocols are sandwich protocols which comprise formation of immobilized or immobilizable complexes in which an analyte is sandwiched between two affinity counterparts. One of the counterparts is analytically detectable and the other immobilized or immobilizable and possibly also analytically detectable. The sandwich complex is measured in step (iii).

Another non-competitive variant utilizes only one affinity counterpart to the analyte in immobilized or immobilizable form. In this case complex formation leads to an immobilized complex, or a soluble complex that subsequently is immobilized. The immobilized complex as such may be measured in step (iii). In one variant the affinity counterpart which is immobilized or immobilizable has been labeled with an analytically detectable group that changes its signal when the analyte binds to the affinity counterpart.

Non-competitive protocols have their greatest potential for molecules that simultaneously can bind two or more affinity counterparts, i.e. large molecules.

Analytically Detectable Reactants.

By the term "analytically detectable" is contemplated that an affinity reactant can be analytically discriminated from other affinity reactants participating in the formation of the complex to be measured in step (iii). Detectability may derive from an inherent property of the reactant, for instance an inherent biological function such as the enzyme activity of an enzyme or Fc-receptor binding activity of various Ig-classes and subclasses, or a separately introduced functionality, e.g. labeling with an analytically detectable tag or label, such as biotin (=affinity label), enzyme, chromogen, fluorogen, fluorophor, chemiluminscent group, radioactive group etc. Detectability also includes that the formed complex is detectable by itself, for instance by changing the optic properties of a solution etc.

A detectable label may be combined with a second label selected such that the labels together give the appropriate signal when the complex is formed or dissociated. This variant may be illustrated with scintilliation proximity assays (SPA) in which a soluble affinity reactant, which is labeled with tritium, is used together with a solid phase comprising a scintillation substance. When the tritium-label becomes incorporated in a complex bound to this kind of solid phase a signal will appear. The principle with interacting labels may also be illustrated with pairs of fluorophores that may be identical or different and with fluorescence-quencher pairs.

An Illustrative Variant of Running Several Samples in Parallel

Step (i): The microfluidic device is as discussed above and comprises k microchannel structures (k is an integer 2 or larger), each of which comprises an immobilized affinity counterpart to an analyte or a combination of such counterparts. The affinity counterparts may or may not differ between the microchannel structures. The affinity counterparts are preferably located to the reaction microcavities in which the affinity complex is to be retained.

Step (ii): A liquid aliquot (aliquot 1) that contains an unknown amount of analyte is introduced into n of the k microchannel structures which contain the affinity counterparts, i.e. aliquot $1^1$ into microchannel structure 1, aliquot $1^2$ into microchannel structure 2 . . . and aliquot $1^n$ into microchannel structure n, where n is an integer equal or smaller than k. Possibly there is also introduced an aliquot containing a known amount of analyte into at least m of the remaining microchannel structures, if any, i.e. aliquot $1^{n+1}$ into microchannel structure n+1, aliquot $1^{n+2}$ into microchannel structure n+2 . . . and aliquot $1^{n+m}$ into microchannel structure n+m, where m is an integer such that n+m is equal or smaller than k. The aliquots with their possible content of analyte are then transported through the microchannel structures such that immobilized complexes will be retained under flow conditions in the reaction microcavity of each microchannel structure. For aliquots that contain no analyte there will be no formation of complex.

Steps (iii) and (iv): The amount of the immobilized complex in each reaction microcavity is measured and related to the amount of analyte in the corresponding starting aliquot/sample.

With respect to reactants and their addition, similar protocols as those discussed above may be used for variants B-F below. In these variants the demand on using limiting and unlimiting amounts may be less important. For alternatives B-D, the concentration and/or relative amounts of the affinity reactants used are typically essentially constant for several of the experiments run in parallel according to the invention. Variants B-F are primarily run under non-diffusion-limiting conditions.

B. Selection of Binders (Analytes) from a Library of Potential Binder Candidates.

Two preferred variants are:

A) Different binder candidates and/or combinations of binder candidates from a library are used in immobilized form in two or more of the microchannel structures of the microfluidic device provided in step (i). A soluble form of a known common ligand is used to form the immobilized complex in step (ii).

B) The same known immobilized ligand is present in two or more of the microchannel structures of the microfluidic device provided in step (i). To each microchannel structure a single binder candidate or a combination of different binder candidates may be introduced into each microchannel structure in step (ii).

A larger extent of complex formation in the reaction microcavity of a particular microchannel structure will suggest that the binder used in this microchannel structure will have a stronger tendency to form an affinity complex than a binder giving a lower extent of complex formation in another microchannel structure. This presumes that other reaction variables are kept essentially constant.

For other variants the meaning of a larger or smaller amount of retained complex in the reaction microcavity will depend on the particular protocol used. For certain protocols a larger amount will suggest a more efficient binder compared to a binder resulting in a smaller amount. For other protocols the opposite will be true.

In both variant (a) and (b) the reaction conditions may or may not differ between the individual microchannel structures.

The preferred protocols are the same as for alternative F below.

Formed affinity complexes can be further characterized with respect to the characteristics of the binder in the complex, for instance structure, binding characteristics, biological function etc.

C. Determination of Immobilization Techniques and/or Solid Phase that are Suitable for a Given Affinity Pair.

In this case at least the immobilization technique for the affinity reactant bound to the solid phase and/or the solid phase as such differ between two or more microchannel structures. The difference may relate to: conditions for physical adsorption, covalent attachment including kind of covalent bridge, affinity reactants used for affinity immobilization, kind of solid phase etc.

The meaning of a larger or smaller amount of retained complex in the reaction microcavity will depend on the protocols used. For certain protocols a larger amount will suggest an immobilization technique and/or a solid phase favoring binding compared to a technique giving smaller amount. For other protocols the opposite will be true.

D. Determination of Suitable Reaction Conditions Related to the Liquid.

In this case at least one reaction variable related to the liquid varies between two or more microchannel structures in the microfluidic device. Typical reaction variables are pH, temperature, ionic strength, amount of an inhibitor or a promotor of complex formation, hydrogen-bond breaking agents, detergents, and flow rate in the microchannel structures etc.

The meaning of a larger or smaller amount of retained complex will depend on the protocols used. For certain protocols a larger amount will suggest an immobilization technique favoring binding compared to a technique giving smaller amount. For other protocols the opposite will be true.

E. Determination of a Ligand and/or a Binder with Respect to their Suitability for Dissociation of their Affinity Complex.

These protocols typically start from microchannel structures in which the complex between the ligand and the binder is predispensed or preformed in immobilized form in the reaction microcavity. The complex may contain an analytically detectable reactant. Upon dissociation of the complex the analytically detectable reactant is released from the complex and the remaining amount of complex can be measured directly in the reaction microcavity or indirectly as the amount of released reactant in a separate detection microcavity positioned downstream the reaction microcavity. Alternatively the affinity counterpart that forms the link to the solid phase comprise a label that change as a function of the release of the other counterpart.

Suitable reaction variables that may be varied are given under "Definitions" above.

F. Determination of Qualitative Aspects of Complex Formation.

The present invention applies to flow conditions during formation or dissociation of affinity complexes on a solid phase that is retained in a reaction microcavity. One can envisage that the distribution of the complex in the solid phase (reaction microcavity) along the flow direction will reflect affinity constants and rates for association and dissociation etc under the conditions used, and that this distribution will depend on various factors such as kind of binder and ligand and their concentrations, and substitution degree and availability on the solid phase, kind of solid phase, pH, ionic strength, flow rate etc.

One can therefore conceive that refined information of qualitative aspects of binding can be accomplished by measuring this distribution, e.g. as the local amount of complex as a function of position in the solid phase (reaction microcavity) along the flow direction.

The requirement on inter-channel variation in residence time is strict, e.g. the variation should be within mean residence time +75%, such as +50% or +25% or +10% or +5%.

A simple case is that one starts with a library of compounds (=binders) in which the individual members are of similar size. The library is then tested according to the invention in a microfluidic device in which two or more of the microchannel structures have the ligand immobilized in the reaction microcavity. Since the compounds are of the same size, the diffusion will be essentially the same for the members of the library. The local amount of complex as a function of position in the flow direction of the solid phase will therefore reflect the affinity between the compound and the ligand that has formed the complex in a particular microchannel structure. A sharp zone, for instance, in the initial part of the solid phase (reaction microcavity) could suggest a stronger affinity than a broader more diffuse zone that is located more downstream.

The distribution of a complex in the solid phase (reaction microcavity) may also be used as a function test for an assay, e.g. of the type discussed for alternative A above.

This innovative alternative requires that the binding reaction between an immobilized ligand and a binder takes place in the reaction microcavity and that the complex formed is measured in step (iii). The immobilized ligand may be introduced prior to formation of the complex. The ligand and binder may be any of the affinity counterparts given above for library members provided the formed complex can be retained in sufficient amount in the reaction microcavity. Typically the immobilized ligand is present in an unlimited amount. To facilitate the measurement in step (iii) properly selected detectable reactants can be included in one or more of steps (i)-(iii), e.g. a) the immobilized ligand may have a label that change its signal upon formation of the immobilized complex, b) the binder may have a label meaning that the complex formed in step (ii) will comprise the label, c) a soluble analytically detectable affinity counterpart to the binder is used in a sandwich protocol etc.

A potentially interesting variant includes that two labels that are interacting with each other when in close proximity are used. A typical example is scintillation proximity assays (SPA) in which the ligand is labeled with tritium and the solid phase comprises a scintillation substance. SPA has found wide-spread use for screening of drug candidates, affinity ligands etc with respect to interaction properties.

Other interesting variants include sandwich protocols and displacement protocols as described above for alternative A with the proviso that the binder in this variant of the invention replaces the analyte.

A soluble analytically detectable affinity counterpart to the binder is preferably used when the binder is large and able to bind two affinity counterparts simultaneously, typically in sandwich protocols. The other labeled reactants that are mentioned above have great advantages for small binders.

In the context of this aspect of the invention, it may be interesting to determine relative affinity of a complex, binder and/or ligand in relation to various members of a library as defined under "Definitions" above.

By adapting the flow rates to implement reactions that are not diffusion-limited the main feature studied will be the affinity constants. This in particular applies to affinity reactants that are large.

Variants meaning that the formed affinity complex as such is determined are also possible to use in this alternative (F).

Samples

The samples used in one run of the innovative method correspond to a collection (library) of samples. At least two of the members of the collection differ with respect to the reaction variable(s) to be characterized.

Samples that differ with respect to reaction variables that are defined by soluble molecular entities can be introduced into the inlet ports of the microchannel structures in step (ii) or in step (iii). In the case the reaction variables are defined by insoluble entities (solid phases, immobilization techniques etc), the library is preferably provided in step (ii) together with the microfluidic device.

Different protocols may require different kind of samples and vice versa.

For alternatives A and B above, the samples are typically derived from biological material such as whole blood, plasma, serum, buffy coat, blood cells, semen, cerebrospinal fluid, lymph, lachrymal fluid, ascites, tissue, supernatants from cell lysates, cell culturing etc that has been treated in various ways in order to give aliquot 1. Included are also biologically material that has been produced synthetically such as synthetically produced oligo- and polypeptides, oligo- and polynucleotides, compounds that potentially are mimicking biological molecules or interactions etc.

For the other alternatives the samples typically are more or less synthetic.

Depending on the particular protocol, alternative F may utilize any of the abovementioned kinds of samples.

Measuring and Characterization (Step (iii) and Step (iv))

The measurement in step (iii) comprises measuring a) the distribution of the affinity complex in the reaction microcavity (solid phase) along the flow direction, or b) the total amount of the complex in the reaction microcavity. The latter includes that measurement is carried out only in a certain part of the reaction microcavity as long as this amount is representative for the total amount. Alternative (a) in particular applies to alternative (F) above.

A number of various ways of measuring immune complexes immobilized to a solid phase by utilizing analytically detectable affinity reactans are known in the field. In principle most of them can be used in the present invention.

Typical examples are spectroscopic methods based on chemiluminescence, bioluminescence, fluorescence with particular emphasis of laser-induced fluorescence (LIF) etc. As indicated elsewhere in this specification these spectroscopic principles often utilize reactants that are labeled with the corresponding analytically detectable group (label). Other principles are based on signals emanating from the complex as such, for instance turbidometry.

As already discussed step (iii) may comprise substeps in which analytically detectable affinity reactants are introduced for facilitating the measurement.

The characterization step (step (iv)) means that the measured value in step (iii) is used to characterize an uncharacterized reaction variable in the samples. This is common practice in the field and needs no further comments. In some cases when the inventive method results in a binding capacity for an unknown entity characterization for identifying the entity may be included in the method aspect of the invention.

The best mode corresponds to the work presented in the experimental part.

A Separate Aspect of the Invention

Figure 3:
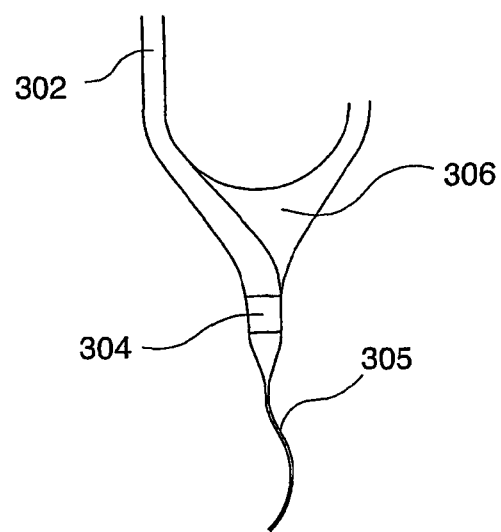
FIG. 3 illustrates the key part of a substructure that comprise a reaction microcavity and means for creating a pressure drop.

A separate aspect of the invention is a structural unit (substructure) for reducing inter-channel variations in flow. The unit is illustrated in FIG. 3. The unit comprises (a) an inlet microconduit (302), (b) a microcavity (304) in which a reaction is to take place under controlled flow conditions, and (c) an outlet microconduit (305). This device is characterized in that there are means for creating a pressure drop in the microcavity (304) and/or in the outlet microconduit (305) downstream the microcavity (304) so that the inter-channel variation in residence time within the microfluidic device for the samples introduced via the inlet microconduits (302) becomes within the limits discussed above. Suitable flow rates through the microcavity are typically within the intervals given above. The means for creating the pressure drop are as outlined in the earlier part of this specification.

In a preferred variant of this inventive aspect there is also an additional microconduit (103 in FIG. 1*a*, 306) merging with the inlet microconduit as illustrated in FIGS. 1*a* and *b*. This additional microconduit may have various functions (vent, inlet etc) and intersects with the inlet microconduit (302), typically in close proximity to its joint with the reaction microcavity (304).

As discussed for FIGS. 1*a* and *b*, and 2 the microchannel structures comprising this preferred substructure can be present in a substrate having an axis of symmetry and arranged so that inlet microconduit (302) and the additional conduit (103 in FIG. 1*a*) are at a larger radial distance than the outlet conduit (305) and the reaction microcavity at an intermediary radial distance (304). The substrate may comprise a plurality of this kind of microchannel structures/substructure oriented radially outwards from the axis of symmetry (spinning axis) and arranged to define two or more annular zones (rings) around the spinning axis, or sectors of such a zone. According to this aspect the microchannel structures in the same annular zone has the substructure at the same radial distance while the substructures for other annular zones are at a different radial distance. Since it is known that the centrifugal force at an outer position is larger than at an inner position, outlet microconduit (105,305) in an outer annular zone shall be longer than in an inner annular zone if the hydrodymanic cross-sectional area is kept constant and the same liquid flow is desired for all the microchannel structures of this kind on the substrate.

Thus by varying the design (hydrodynamic cross-sectional area and/or length) it is possible to place several microchannel structures comprising the described substructure at different radial distances while maintaining the same flow rate through the reaction microcavity. Inversely this concept makes it possible to construct microfluidic devices in which there are microchannel structures in which the flow rate through the reaction microcavity will differ in a well-defined manner.

This aspect of the invention is useful in the method aspect of the invention (method for the characterization of reaction variables). This aspect may also be useful for other microfluidic applications where a controlled liquid flow is beneficial, e.g. microtitration and chemical synthesis in the microformat and other situations where controlled mixing or controlled addition of reagents are needed.

The patent applications given below have been discussed in this specification. All of them are hereby incorporated by reference, in particular those WO applications that designate the US.

WO 9116966, 9615576, WO 9721090, WO 9800709, 9807019, WO 9958245, WO 0056808, WO 0146465, WO 0147637, WO 0154810, WO 0185602, U.S. Ser. No. 60/315,471 and corresponding International Patent Application, U.S. Ser. No. 60/322,622 and the c.i.p. U.S. application filed on Jan. 31, 2002.

Experimental Part

FIGS. 1-2 shows the structure used in this experiment. A complete myoglobin assay was performed in a disc of the same dimension as a compact disc (CD). In the disc used there were 24 similar structures (101,201) in parallel and the structures were divided in 2 sets each containing 12 structures (only one set is shown in FIG. 2). A common distribution channel (119, 219) connected the 12 structures, through which buffer and reagents were distributed to the 12 reaction structures via either inlet port (209) or inlet port (210). Every structure had also its individual inlet unit (108,114) designed with a sample receiving structure (111), which has a volume definition function. The dimensions of the channel are indicated in FIGS. 1a-b.

In order to achieve capillary action in the reaction structures the CD surface was treated with $O_2$-plasma, subsequently a plastic lid was laminated to the CD. According to a standard procedure all structures were incubated with PEG-PEI WO 0056808 (Gyros AB) and WO 0147637 (Gyros AB). The PEG-PEI molecules bind to the surface and establish a layer with low protein adsorption. After the PEG-PEI incubation the structures were thoroughly washed with water.

The immunoassay was performed in an automated system. The system (instrument prototype, Gyros AB, Uppsala, Sweden) was equipped with CD-spinner, holder for Microtiter plates (MTP) and a robotic arm with a holder for a capillary connected to a syringe pump and 8 slit pins. The capillary transferred all reagents and buffers from a MTP to either of the two inlet units (209,210) of the common distribution channel (119) in the disc. The slit pins transferred individual samples from a MTP to the individual sample inlet units (108) in the disc.

The instrument prototype is a fully automated robotic system controlled by application-specific software. Microplates containing samples or reagents are stored in a carousel within the system. A high precision robot transfers samples from microplates or containers into the microworld of the CD. CDs are moved to the spinning station for the addition of samples and reagents. An application-specific method within the software controls the spinning at precisely controlled speeds controls the movement of liquids through the microstructures as the application proceeds.

Polystyrene particles (15 μm, Dynal Particles AS, Norway) were selected for the solid phase. The beads was modified by passive adsorption of phenyl-dextran to create a hydrophilic surface and were subsequently covalently coupled with a monoclonal antimyoglobin 8E.11.1 (LabAs, Tartu,Estonia) using CDAP chemistry (Kohn & Wilchek, Biochem. Biophys Res. Comm. 107 (1982) 878-884).

After coupling with the antibody, a suspension of the particles was distributed in the common distribution channel (119) via inlet unit (109) and moved through the structure by centrifugal force. The centrifugal force combined with the vents (122) divide the suspension in the channel in equal portions each of which forms a bed of packed particles (column) in the reaction microcavity (104) against the dual depth in front of the outlet conduit (105). The approximate volume of the column was 10 nl. The columns were washed once with 0.01 M Phosphate-buffer, pH 7.5 containing 0.15 M NaCl via the common distribution channel (119). Every addition of solution delivers 200 nl liquid to the individual column. One addition of washing solution is 20 times the column volume, which ensures a very efficient washing To demonstrate the myoglobin assay in the system a 6-point standard curve was created. The myoglobin samples (diluted in PBS, 1% BSA) with concentrations in the range of 0-1620 ng/ml where distributed to the individual inlet units by slit pins. The sample volume 100 nl was defined in the sample receiving structure (111) (during the first two step in the spin flow method). To reach favourable kinetic condition under the capturing step (for myoglobin to bind) the flow rate of the sample should not exceed 1 nl/sec. The sample flow rate was controlled by the spin velocity (spin flow 1). After sample capturing the columns were washed twice by addition of PBS, 0.01% Tween to the common distribution channel followed by a spin step. Detection antibodies in excess were applied next via the common distribution channel, these were monoclonal antimyoglobin 2F9.1 (LabAs,Tartu) and a similar slow flow rate (spin flow 2) was used. The detecting antibodies were labelled with a fluorophor Alexa 633 (Molecular Probes, Eugene, USA). Excess of labelled antibody was washed away in 4 additions of PBS-T.

Figure 4:
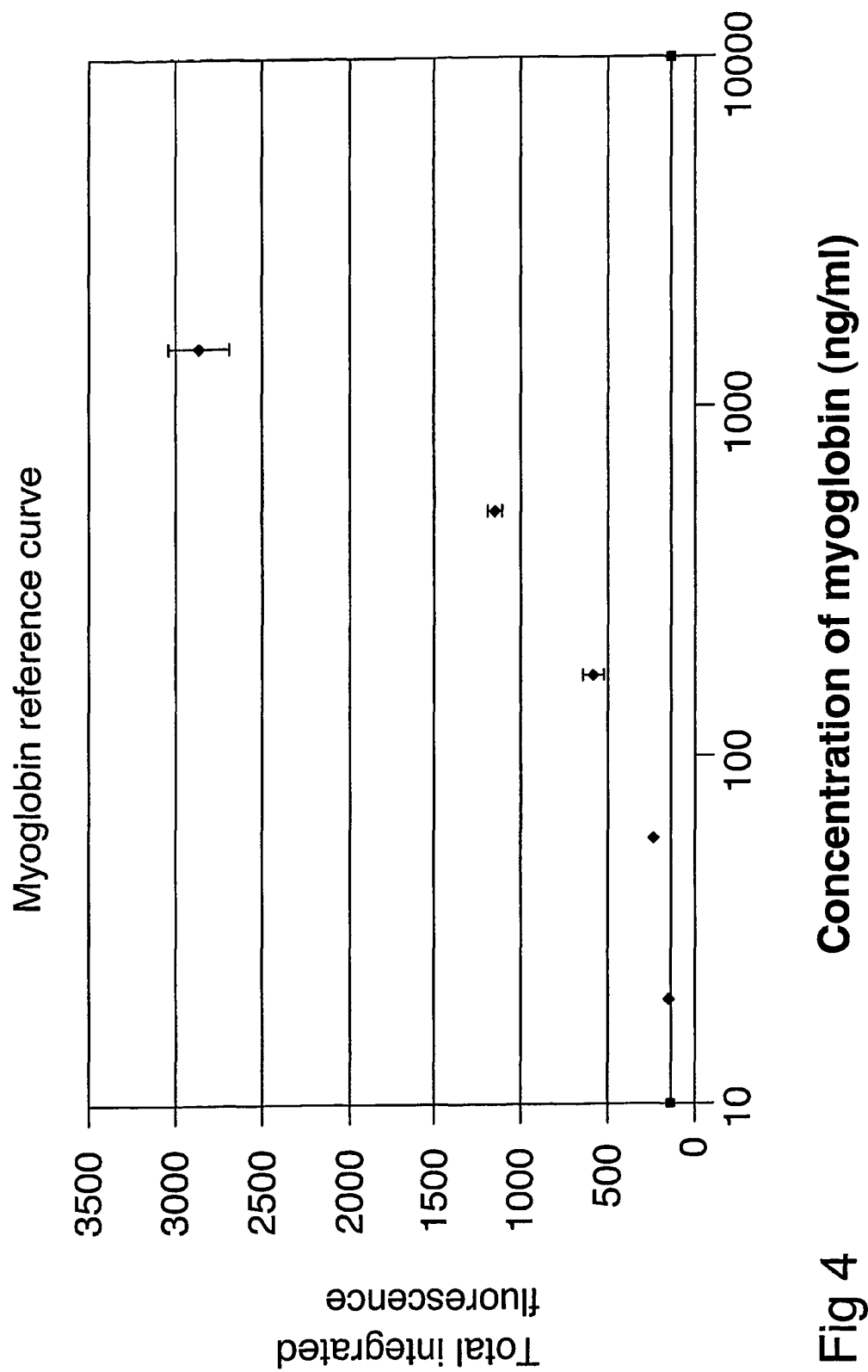
FIG. 4 represents the results obtained in the experimental part.

The completed assay was analysed in a laser induced fluorescence (LIF) detector. The detector moved radially along the column while the disc was rotating. The results are presented in FIG. 4. Signal intensity was typically concentrated to the top of the column.

The design of the Laser Induced Fluorescence (LIF) module was constructed for quantitative measurement of fluorescence in the microfluidic device (disc of CD format) used in the experiments.

The disc was rotated by means of a motor on a rotatable shaft; the speed could be varied from 60 to 3000 rpm. By means of an encoder and a fixed home position on the CD the position of each structure of interest could be stored in a file.

A pick-up head was constructed. It consisted of a laser whose beam was reflected on a dichroic mirror and focused onto the structure of interest in the disc through a 5× objective. The epi-fluorescent light passed through the dichroic mirror and through a band-pass filter, optimised for the flourochrome at hand. It was focused onto a PMT by means of an aspheric lens.

By rotating the disc while measuring a signal across the structure a trace was obtained corresponding to the fluorescence in the structure. By moving the pick-up means of a motor in radial direction while rotating the disc a measurement of the total fluorescence in the structure was obtained.

The detector is described in U.S. Ser. No. 60/322,622, SE 0103118-6, SE 010446-9 and US application filed on Jan. 31, 2002 ("Arrangement and method for measurement in spinning microfluidic devices").

An overview of the run method in the system is presented in Tab 2.

TABLE 1

An overview of the run method performed in the system

| Run method | Spin profile |
|---|---|
| Wash of CD structures | |
| Spin1 Transfer of beads | 5700 rpm 15 s |
| Spin2 Wash of beads | 4500 rpm 10 s, 5000 rpm 10 s |
| Spin3 Transfer of samples | 5800 rpm 15 s, 6700 rpm 5 s |
| Spin flow1 | 1200 rpm 2 s, 2200 rpm 0.5 s, from 1700-2500 rpm in 90 sec. 3000 rpm 15 s, 5500 rpm 5 s |
| Myoglobin wash 1 | |
| Spin4 Myoglobin wash 2 | 4500 rpm 20 s, 5700 rpm 5 s |
| Spin5 Transfer of conjugate | 4500 rpm 20 s, 5700 rpm 5 s |
| Spin flow 2 | 2500 rpm 0.6 s, 1500-2500 rpm in 120 sec. 3000 rpm 15 s, 5500 rpm 5 s |
| Conjugate wash1 | |
| Spin6 Conjugate wash2 | 4500 rpm 20 s, 5700 rpm 5 s |
| Spin7 Conjugate wash3 | 4500 rpm 20 s, 5700 rpm 5 s |
| Spin8 Conjugate wash4 | 4500 rpm 20 s, 5700 rpm 5 s |
| Spin9 Detection | 4500 rpm 20 s, 5700 rpm 5 s |

Certain innovative aspects of the invention is defined in more detail in the appending claims. Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A microscale method of characterizing the strength of the affinity between a compound, or combination of compounds, and an immobilized ligand which have affinity for each other, comprising the steps of:
   (i) providing a microfluidic device comprising a microchannel structure comprising a reaction microcavity, said reaction microcavity comprising a solid phase to which the ligand is immobilized, wherein a) the microfluidic device comprises a substrate having an axis of symmetry and b) the microchannel structure is oriented radially relative to the axis of symmetry wherein the reaction microcavity is oriented at a larger radial distance from the axis of symmetry than a substructure delivering liquid to the reaction microcavity;
   (ii) introducing under flow conditions a sample containing the compound or combination of compounds into a reaction microcavity of the microchannel structure to form immobilized complexes of the compound or compounds with the ligand along the solid phase of the reaction microcavity, wherein the substrate is spun around its axis of symmetry to drive liquid within the microchannel structures;
   (iii) measuring the distribution of the formed complexes in the solid phase within said reaction microcavity along the flow direction of the solid phase, and
   (iv) determining the strength of the affinity between a compound, or combination of compounds, and the immobilized ligand based on the distribution of the formed complexes in the flow direction of the solid phase.

2. The method according to claim 1, wherein the immobilized ligand is present in excess.

3. The method according to claim 1, wherein step (ii) is performed under non-diffusion limiting conditions.

4. The method according to claim 1, wherein the compound or compounds are selected from nucleotides, oligonucleotides, polynucleotides, amino acids, oligopeptides, polypeptides, proteins, lipids, and carbohydrates.

5. The method according to claim 1, wherein characterizing the affinity between the compound or compounds and the ligand is further defined as characterizing the formation or dissociation of the formed immobilized complex.

6. The method according to claim 1, wherein prior to step (iii) the method comprises dissociating under flow conditions the immobilized form of the complex within the reaction microcavity.

7. The method according to claim 1, wherein the sample contains a combination of compounds, wherein a compound is analytically discriminated from other compounds based on an inherent property of the compound.

8. The method according to claim 7, wherein the inherent property comprises an inherent biological function.

9. The method according to claim 8, wherein the inherent biological function comprises Fc-receptor binding activity of various Ig-classes and subclasses.

10. The method according to claim 1, wherein the microfluidic device comprises a plurality of microchannel structures that are under common flow control, and wherein the method is performed essentially in parallel in each of two or more of the plurality of microchannel structures.

11. The method according to claim 10, wherein the microchannel structures comprises a flow restriction downstream of the reaction microcavity, which creates a pressure drop that restricts the flow through the reaction microcavity.

12. The method according to claim 10, wherein step (iii) comprises determining the distribution of the complex along the flow direction in the reaction microcavity in each of said two or more microchannel structures.

13. The method according to claim 10, wherein prior to step (iii) the method comprises subjecting under flow conditions said immobilized complex to at least one reaction condition, said at least one reaction condition being different or uncharacterized for said two or more microchannel structures.

14. The method according to claim 13, wherein said at least one reaction condition that varies between the microchannel structures comprises pH, temperature, ionic strength, amount and kind of denaturing agents, liquid flow, immobilization techniques or solid phases.

* * * * *